United States Patent [19]

Brown et al.

[11] Patent Number: 5,990,366
[45] Date of Patent: Nov. 23, 1999

[54] SELECTIVE XYLENE DISPROPORTIONATION PROCESS FOR PSEUDOCUMENE PRODUCTION

[75] Inventors: Stephen H. Brown, Princeton; David L. Stern, Mount Laurel, both of N.J.

[73] Assignee: Mobil Oil Corporation, Fairfax, Va.

[21] Appl. No.: 09/218,580

[22] Filed: Dec. 22, 1998

[51] Int. Cl.$^6$ .................................................. C07C 5/22
[52] U.S. Cl. ............................................................ 585/475
[58] Field of Search ...................................... 585/475, 470

[56] References Cited

U.S. PATENT DOCUMENTS

| | | | |
|---|---|---|---|
| 3,721,717 | 3/1973 | Suld et al. | 260/672 T |
| 3,784,621 | 1/1974 | Suggit et al. | 260/672 T |
| 3,915,895 | 10/1975 | Suggit et al. | 252/455 Z |
| 4,038,335 | 7/1977 | Minachev et al. | 260/672 T |
| 4,090,981 | 5/1978 | Rodewald | 252/455 Z |
| 4,127,616 | 11/1978 | Rodewald | 260/671 R |
| 4,465,886 | 8/1984 | Rodewald | 585/467 |
| 4,477,583 | 10/1984 | Rodewald | 502/71 |
| 4,891,467 | 1/1990 | Sikkenga | 585/467 |
| 4,950,835 | 8/1990 | Wang et al. | 585/467 |
| 5,004,854 | 4/1991 | Yan | 585/489 |
| 5,234,872 | 8/1993 | Apelian et al. | 502/62 |
| 5,238,677 | 8/1993 | Apelian et al. | 423/714 |
| 5,243,117 | 9/1993 | Chang et al. | 585/467 |
| 5,403,800 | 4/1995 | Beck et al. | 502/64 |
| 5,406,015 | 4/1995 | Beck et al. | 585/475 |
| 5,476,823 | 12/1995 | Beck et al. | 502/60 |
| 5,625,103 | 4/1997 | Abichandani et al. | 585/475 |
| 5,659,098 | 8/1997 | Beck et al. | 585/475 |

OTHER PUBLICATIONS

Ockerbloom, "Xylenes and Higher Aromatics" Hydrocarbon Processing, Apr. 1972, pp. 114–118.

*Primary Examiner*—Walter D. Griffin
*Assistant Examiner*—Thuan D. Dang
*Attorney, Agent, or Firm*—Peter W. Roberts; Malcolm D. Keen

[57] ABSTRACT

There is provided a process for shape selective xylene disproportionation that involves contacting a feedstream which includes xylene under conversion conditions, with a molecular sieve catalyst that has been surface modified. The xylene disproportionation process has a selectivity for pseudocumene of over 85%.

7 Claims, No Drawings

5,990,366

SELECTIVE XYLENE DISPROPORTIONATION PROCESS FOR PSEUDOCUMENE PRODUCTION

BACKGROUND OF THE INVENTION

The present invention is directed to a shape-selective xylene disproportionation process over a surface modified molecular sieve catalyst to selectively form pseudocumene.

The term "shape-selective catalysis" describes the catalytic selectivities found in molecular sieves such as zeolites. The principles behind shape selective catalysis have been reviewed extensively, e.g., by N.Y. Chen, W. E. Garwood and F. G. Dwyer, *Shape Selective Catalysis in Industrial Applications*, 36, Marcel Dekker, Inc. (1989). Within a zeolite pore, hydrocarbon conversion reactions such as paraffin isomerization, olefin skeletal or double bond isomerization, oligomerization and aromatic disproportionation, alkylation or transalkylation reactions are governed by constraints imposed by the channel size. Reactant selectivity occurs when a fraction of the feedstock is too large to enter the zeolite pores to react; while product selectivity occurs when some of the products cannot leave the zeolite channels. Product distributions can also be altered by transition state selectivity in which certain reactions cannot occur because the reaction transition state is too large to form within zeolite pores or cages. Another type of selectivity results from configurational restraints on diffusion where the dimensions of the molecule approach that of the zeolite pore system. A small change in the dimensions of the molecule or the zeolite pore can result in large diffusion changes leading to different product distributions. This type of shape selective catalysis is demonstrated, for example, in selective toluene disproportionation to para-xylene as disclosed in U.S. Pat. No. 5,659,098 to Beck et al. Another example of shape selective catalysis, ethylbenzene disproportionation, is disclosed in U.S. Pat. No. 5,406,015 to Beck et al.

Xylenes and higher aromatics such as pseudocumene and mesitylene are desired commercial products having various uses as disclosed in N. E. Ockerbloom's article, "Xylenes and Higher Aromatics" in *Hydrocarbon Processing*, April 1972, pg. 114–118. This article discloses that these products can be obtained through fractional distillation or extraction from $C_9$ aromatic fractions obtained from naphtha cracking or reformate. Pseudocumene may be oxidized to form trimellitic acid which is useful in the manufacture of synthetic fibers and plastics. It may also be desirable to manufacture the acid anhydride form. Thus, there have been efforts to devise processes resulting in a high purity pseudocumene product. Fractionation of an extracted, heavy catalytic reformate containing about 40% pseudocumene to obtain purified pseudocumene requires large fractionation towers to perform the separation. Using a crystalline zeolite catalyst on an extracted reformate cut to increase pseudocumene content has been proposed in U.S. Pat. No. 5,004,854 to Yan.

Synthesis of pseudocumene by methylation of benzene or methyl-substituted benzenes is disclosed as producing a higher than equilibrium concentration of pseudocumene in U.S. Pat. No. 4,891,467 to Sikkenga. However, the requirement of a methanol feedstock limits the practical application of such a process. U.S. Pat. No. 3,784,621 to Suggitt discloses a process whereby toluene is contacted with a disproportionation catalyst, a $C_8$ aromatic fraction is then separated, and the $C_8$ aromatic fraction is then contacted with a disproportionation catalyst to form a $C_9$ aromatic fraction. The $C_9$ aromatic fraction may contain pseudocumene and/or mesitylene. Disproportionation of orthoxylene to produce primarily mesitylene is disclosed by Suggitt et al in U.S. Pat. No. 3,915,895. U.S. Pat. No. 4,038,335 to Minachev et al discloses a catalytic xylene disproportionation process yielding on the order of 68% to 69% pseudocumene, relative to all trimethylbenzene isomers.

It would be desirable to produce a high purity pseudocumene product via a xylene disproportionation process amenable to a wide variety of xylene feeds including single isomer feeds, equilibrium mixtures and para depleted feeds without the requirement of special feedstocks and/or operating conditions, and without the need for further purification to increase the pseudocumene content of the product.

SUMMARY OF THE INVENTION

The present invention provides a process for disproportionation of xylene to selectively form pseudocumene. In the process, the feed comprises xylene and is contacted with a surface modified molecular sieve catalyst under disproportionation conditions. The disproportionation process yields a product comprised of toluene, pseudocumene (1,2,4 trimethylbenzene), mesitylene (1,3,5 trimethylbenzene) and hemimellitene (1,2,3 trimethylbenzene). Pseudocumene is selectively formed in the shape selective catalytic reaction of the invention and is at least about 85 weight percent of the three trimethylbenzene isomers produced. The surface modification of the catalyst of the invention reduces the activity or acidity of the catalyst surface. Accordingly, the surface modification of the catalyst is sufficient to prevent pseudocumene yield loss as a result of pseudocumene conversion at the catalyst surface. Pseudocumene selectivity of over 96% may be obtained using the process of the invention. The surface modification of the catalyst may comprise at least one step of contacting the catalyst with a selectivating agent and/or a surface modification agent such as a polymer or compound containing silicon, a carboxylic acid, other carbon containing compounds at higher than process temperature, a nitrogen containing compound or an inorganic oxide. The process of the invention obtains high pseudocumene yields with xylene feeds having a single isomer (ortho, meta or para), equilibrium mixtures of isomers, or non-equilibrium mixtures such as a para depleted feed stream from a para xylene recovery unit. In embodiments of the invention, the xylene feed is isomerized to substantially equilibrium concentrations and then the isomerized xylene feed is disproportionated to selectively produce pseudocumene without the need for further purification to increase the pseudocumene content of the product.

DETAILED DESCRIPTION OF THE INVENTION

The present invention relates to a xylene disproportionation process which selectively forms a least about 85 weight percent pseudocumene, relative to the total amount of trimethylbenzene isomers produced.

In embodiments of the invention, the catalysts used for performing the xylene isomerization process are those high in xylene disproportionation activity and low in xylene isomerization activity. Such molecular sieve catalysts combine shape selectivity to selectively form pseudocumene within the catalyst with surface modification to prevent the reconversion of pseudocumene product to other compounds on the catalyst surface. For example, silica selectivated molecular sieve catalysts are preferred, and 1×–3× ex-situ silica selectivated catalysts are especially preferred. Other surface modified molecular sieve catalysts are effective in the process of the invention, and may be prepared by processes such as ex-situ and/or in-situ selectivation, coking selectivation, and treatment with inorganic modifiers in order to obtain surface modification of the molecular sieve, or any combination of such selectivation or treatment processes.

The catalytic molecular sieves useful herein have a Constraint Index from about 1 to about 12 and include intermediate pore zeolites as well as other crystalline inorganic materials such as ALPO's or SAPO's. Zeolites which conform to the specified values of Constraint Index for intermediate pore zeolites include ZSM-5, ZSM-11, ZSM-5/ZSM-11 intermediate, ZSM-12, ZSM-22, ZSM-23, ZSM-35, ZSM-48, ZSM-50, and ZSM-57. Such zeolites are described, for example, in U.S. Pat. Nos. 3,702,886 and Re. No. 29,949, 3,709,979, 3,832,449, 4,046,859, 4,556,447, 4,076,842, 4,016,245, 4,229,424, 4,397,827, 4,640,849, 4,046,685, 3,308,069 and Re. No. 28,341, to which reference is made for the details of these zeolites. The details of the method by which Constraint Index is determined are described fully in the U.S. Pat. No. 4,016,218, incorporated herein by reference.

In the process of the present invention, a molecular sieve, for example a zeolite, either incorporated with a binder or in unbound form, may be impregnated with a selectivating agent at least once (1×), and preferably less than four times (4×). In embodiments of the invention, the selectivating agent comprises a compound or polymer containing a main group or transition metal, preferably silicon. In each phase of the selectivation treatment, the selectivating agent is deposited on the external surface of the catalyst by any suitable method. For example, the selectivating agent, such as a silicon compound, may be dissolved in a carrier, mixed with the catalyst, and then dried by evaporation or vacuum distillation. This method is termed "impregnation". The molecular sieve may be contacted with the silicon compound at a molecular sieve/silicon compound weight ratio of from about 100/1 to about 1/100.

The silicon compound employed may be in the form of a solution, an emulsion, a liquid or a gas under the conditions of contact with a molecular sieve. The deposited silicon compound extensively covers, and resides substantially exclusively on, the external surface of the molecular sieve. Examples of methods of depositing silicon on the surface of the zeolite are found in U.S. Pat. Nos. 4,090,981, 4,127,616, 4,465,886, 4,477,583, 4,950,835, 5,243,117, 5,403,800, 5,406,015, 5,476,823 and 5,659,098, which are incorporated by reference herein.

The catalysts of the present invention may be ex-situ selectivated as described in the above-referenced U.S. Pat. Nos. 5,406,015, 5,476,823 and 5,659,098 to Beck et al. The selectivation processes disclosed in these three Beck patents require multiple coatings, however, as disclosed above, in the process of the present invention ex-situ single selectivated catalysts may be used. Each coating with a selectivation agent is followed by a calcination step. The catalysts of the present invention may also be in-situ selectivated with a silicon compound by a process of "trim-selectivation" as described in U.S. Pat. No. 5,705,726 which is incorporated by reference herein.

Although the molecular sieve catalysts of the present invention may be selectivated multiple times, as the level of selectivation increases there is a tendency toward ethylbenzene production and away from pseudocumene production. Thus, in embodiments of the invention wherein low levels of ethylbenzene are desirable, the level of selectivation effective to prevent reconversion of pseudocumene on the catalyst surface is balanced against the need to avoid a level of selectivation which results in undesirable ethylbenzene levels in the product stream.

Useful selectivating agents include, organic silicon compounds such as phenylmethyl silicone, dimethyl silicone, and blends thereof. Other silicon compounds, including silanes and alkoxy silanes, such as tetramethoxy silane, may also be utilized. Preferred silicon-containing selectivating agents include dimethylphenylmethyl polysiloxane (e.g., Dow-550) and phenylmethyl polysiloxane (e.g., Dow-710). Dow-550 and Dow-710 are available from Dow Chemical Co., Midland, Mich.

Preferably, the kinetic diameter of the selectivating agent is larger than the zeolite pore diameter, in order to avoid entry of the selectivating agent into the pore and any concomitant reduction in the internal activity of the catalyst.

Examples of suitable carriers for the selectivating silicon compound include alkanes having five or more, preferably seven or more carbons and with a boiling point greater than about 70° C. Optionally, mixtures of low volatility organic compounds, such as hydrocracker recycle oil, may be employed as carriers. The most preferred low volatility hydrocarbon carriers of silicon selectivating agents are decane and dodecane.

Following each deposition of the silicon compound, the catalyst is calcined to decompose the molecular or polymeric species to a solid state species. After the selectivation sequence is complete the catalyst may be subjected to steam treatment if desired to improve selectivity. The calcination and steaming steps may be performed in the manner disclosed in the above-referenced U.S. Pat. Nos. 5,406,015, 5,476,823 and 5,659,098 to Beck et al. If desired, after ex-situ selectivation, in-situ selectivation by silicon containing compounds wherein the silicon compound decomposes to deposit additional silica on the catalyst may be performed as disclosed in U.S. Pat. Nos. 5,406,015 and 5,476,823.

Factors which affect the amount of silica incorporated with the molecular sieve during ex-situ selectivation include temperature, concentration of the silicon compound in the carrying medium, the degree to which the zeolite has been dried prior to contact with the silicon compound, and calcination of the zeolite. Of course, additional silica may be incorporated if in-situ selectivation is performed after ex-situ selectivation. Alternatively, in-situ selectivation with silicon containing compounds may be the only means used to incorporate silica with the molecular sieve.

Alternatively, the catalyst, prior to contacting with xylene under disproportionation conditions, may be subjected to in-situ coking selectivation with a thermally decomposable organic compound at an elevated temperature in excess of the decomposition temperature of said compound but below the temperature at which crystallinity of the zeolite is adversely affected. Generally, this temperature will be less than about 650° C. Typically, coking selectivation is conducted at conditions outside the operating parameters used during the main time span of the catalytic cycle. When the desired coke deposition has been effected, the xylene containing feed is contacted with the coke-containing catalyst under process conditions conducive to disproportionation, with a greatly reduced coking rate. For example, the catalysts of the present invention may be ex-situ selectivated with silicon compound, followed by in-situ coking selectivation as described in U.S. Pat. No. 5,625,103, which is incorporated by reference herein.

As discussed above, treatment with inorganic modifiers in order to obtain surface modification of the molecular sieve is also an effective means to prepare a catalyst for the xylene disproportionation process in accordance with the present invention. Other means suitable for accomplishing surface modification of the shape selective molecular sieve catalyst in accordance with the present invention include, for example, surface treatment with a dicarboxylic acid, such as oxalic acid, to reduce surface acidity without a significant reduction in overall activity as disclosed in U.S. Pat. Nos. 5,234,872 and 5,238,677 to Apelian et al, the disclosures of which are incorporated herein by reference. Reducing the surface acid catalytic activity by chemisorption of a surface deactivating agent having an average cross section of about 5 Angstroms or more such as bulky amines, phosphines, phenols, polynuclear hydrocarbons, cationic dyes, metal compounds or large complex cations is disclosed in U.S. Pat. No. 5,015,361 to Anthes, et al., which is incorporated herein by reference.

While not wishing to be bound by theory, it is believed that the advantages of the present invention are in part obtained by rendering acid sites on the external surfaces of the catalyst substantially inaccessible to reactants, while increasing catalyst tortuosity. Acid sites existing on the external surface of the catalyst are believed to isomerize the solution-phase pseudocumene formed inside the shape selective catalyst toward an equilibrium level with the other two trimethylbenzene isomers, mesitylene and hemimellitene, that is, a mixture of trimethylbenzene isomers comprising less than about 70% weight percent pseudocumene. By reducing the availability to and/or the effectiveness of these acid sites to convert the solution-phase pseudocumene, the relatively high proportion of the pseudocumene (1,2,4 trimethylbenzene) isomer relative to the mesitylene (1,3,5 trimethylbenzene) and hemimellitene (1,2,3 trimethylbenzene) isomers can be maintained and the exceptionally high pseudocumene yields attainable with the process of the present invention are achieved.

The invention also comprises the selective conversion of xylene to pseudocumene by disproportionating xylene in a reaction stream containing a xylene feed with a surface modified catalytic molecular sieve, optionally in the presence of hydrogen, and at reaction conditions suitable to provide pseudocumene selectivity of greater than about 85%, preferably greater than 90%. The product stream may also contain small amounts of the mesitylene (1,3,5 trimethylbenzene) and hemimellitene (1,2,3 trimethylbenzene) isomers and trace amounts of impurities.

As used herein, the term "pseudocumene selectivity" means the proportion of pseudocumene, indicated as a percentage, of all of the trimethylbenzene isomers in the product stream, i.e., pseudocumene (1,2,4 trimethylbenzene), mesitylene (1,3,5 trimethylbenzene) and hemimellitene (1,2,3 trimethylbenzene).

In general, catalytic conversion conditions to perform the xylene disproportionation process of the invention include passing the xylene containing feed over a catalyst according to the invention at a temperature of from about 100° C. to about 760° C., a pressure of from about 0.1 atmosphere (bar) to about 200 atmospheres (bar), a weight hourly space velocity of from about 0.08 to about 2000, and a hydrogen/organic, e.g., hydrocarbon compound, mole ratio of from 0 to about 100.

As explained in greater detail herein, the present invention provides a process for obtaining pseudocumene at xylene conversions of at least 10%, preferably at least about 15–25%, with a pseudocumene selectivity of at least about 85%, preferably at least 90%. Remarkably, pseudocumene selectivities of 95% or 96% or greater may be achieved by the process according to the invention. In embodiments of the invention, the pseudocumene selectivity may be tailored to meet a certain product slate requirement, i.e., incremental adjustments on the order of 0.5% to 1.0% within the above mentioned pseudocumene selectivity range are attainable by adjusting process conditions. For example, if a pseudocumene selectivity of 88.5%, 92% or 95.5% is desired, then the process may be adjusted to provide that pseudocumene selectivity.

The xylene feedstock preferably includes about 50% to 100% xylene, more preferably at least about 80% xylene. The process of the invention obtains high pseudocumene selectivity with xylene feeds comprising a single xylene isomer (i.e., ortho, meta or para) or equilibrium mixtures of isomers. In other embodiments of the invention, non-equilibrium mixtures of xylenes may be used as feed such as a para-depleted effluent stream from a para xylene recovery unit. Other aromatic compounds such as benzene and other alkyl-substituted benzenes may also be present in the xylene feedstock without adversely affecting the present invention.

In embodiments of the invention, an additional xylene isomerization step may be performed wherein the xylene feed is isomerized to substantially equilibrium concentrations, or alternately isomerized to form a para-enriched xylene feed, and then the isomerized xylene feed is disproportionated to selectively form pseudocumene in accordance with the process of the invention as described herein.

The xylene feedstock may also be dried, if desired, in a manner which will minimize moisture entering the reaction zone. Numerous methods known in the art are suitable for drying the xylene charge for the process of the invention. These methods include percolation through any suitable desiccant, for example, silica gel, activated alumina, molecular sieves or other suitable substances, or the use of liquid charge dryers.

The catalytic molecular sieves useful in accordance with the methods of the present invention are preferably in the hydrogen form, prior to modification, but may be in the ammonium or sodium form. The crystal size of zeolites used herein is preferably greater than 0.1 micron, more preferably in the range of 0.1 micron to 0.5 micron. The catalyst in the present invention preferably has an alpha value greater than 1, for example, from about 1 to about 2000. The alpha value of the catalyst may be increased by initially treating the catalyst with nitric acid or by mild steaming before pre-selectivation. This type of steaming is discussed in U.S. Pat. No. 4,326,994. Further discussion regarding the methods of determining the alpha value and crystal size of a catalyst is available in the above-referenced U.S. Pat. Nos. 5,406,015, 5,476,823 and 5,659,098 to Beck et al.

The silica to alumina ratio of the catalysts of the invention may be determined by conventional analysis. This ratio is meant to represent, as closely as possible, the ratio in the rigid atomic framework of the molecular sieve crystal and to exclude aluminum in the binder or in cationic or other form within the channels. Although molecular sieves with a silica to alumina ratio of up to about 10,000 are useful, it is preferred to use zeolites having ratios of at least about 20 to about 2000, more preferably at least about 20 to about 100.

For the improved xylene disproportionation process of this invention, the suitable molecular sieve may be employed in combination with a support or binder material such as, for example, a porous inorganic oxide support or a clay binder. While the preferred binder is silica, other non-acidic binder materials may be employed, generally in the form of dried inorganic oxide gels or gelatinous precipitates. Suitable clay materials include, by way of example, bentonite and kieselguhr. The relative proportion of suitable crystalline molecular sieve to the total composition of catalyst and binder or support may be from about 30% to about 98% by weight, and is preferably from about 50% to about 80% by weight of the composition. The composition may be in the form of an extrudate, beads or fluidizable microspheres.

As discussed above, operating conditions employed in the process of the present invention will affect the pseudocumene selectivity and xylene conversion. Such conditions include the temperature, pressure, space velocity, molar ratio of the reactants, and the hydrogen to hydrocarbon mole ratio ($H_2$/HC). For example, it has been observed than an increase in temperature can substantially increase the conversion of xylene, without significantly reducing pseudocumene selectivity. In addition, it has been observed that the xylene disproportionation process may be performed using $H_2$ as a diluent, thereby reducing aging and thus increasing the cycle length of the catalyst.

In preferred embodiments of the invention, a surface modified molecular sieve catalyst in accordance with the invention is contacted with a xylene feedstock under conditions for effecting vapor-phase disproportionation. Conditions effective for accomplishing the high pseudocumene selectivity and acceptable xylene disproportionation conversion rates include a reactor inlet temperature of from about 200° C. to about 600° C., preferably from 300° C. to about 475° C.; a pressure of from about atmospheric to about 5000 psia, preferably from about 100 to about 1000 psia; a WHSV of from about 0.1 to about 20, preferably from about 2 to about 10; and a $H_2$/HC mole ratio of from about 0.05 to about 20, preferably from about 0.5 to about 6. This process may be conducted in either batch or fluid bed operation, with the attendant benefits of either operation readily obtainable. The effluent from the xylene disproportionation process of the invention may be distilled to yield a trimethylbenzene fraction with a very high pseudocumene content, for example 90% or greater. Also, in a process scheme where a xylene isomerization reactor is present, the effluents from the xylene isomerization reactor and the process of the invention may be combined for downstream separation. The relatively high purity of pseudocumene attained by the process of the invention reduces, and in some instances eliminates, the need for further purification of the pseudocumene before it is processed to make other products, such as the oxidization of pseudocumene to form trimellitic acid.

EXAMPLES

The following non-limiting Examples illustrate the xylene disproportionation process according to the invention.

Example 1

A once-selectivated catalyst (1x) was prepared by contacting a batch of silica-bound H-ZSM-5 preparation (65% ZSM-5/35% $SiO_2$) with a 7.8 weight percent solution of dimethylphenylmethyl polysiloxane (Dow-550) in decane. The decane solvent was stripped off the catalyst. The catalyst was then calcined under nitrogen, followed by air. The temperature of the furnace was elevated to about 540° C. and was maintained at that temperature.

Example 2

A xylene disproportionation run utilizing the catalyst prepared in Example 1 was conducted in an automated unit. The results are reported in Table 1 for two specific reaction temperatures. The unit has an automated sample feature with an on-line gas chromatograph (GC) for characterization of the entire product effluent. Approximately 2.0 grams of the catalyst were loaded into a 0.375" diameter, stainless steel reactor with sand as an inert packing material. The catalyst was heated to reaction temperature under nitrogen atmosphere.

The xylene disproportionation run was initiated by introducing pure para-xylene feed at a $H_2$/HC ratio of 1.0 and a weight hourly space velocity of 3. For each reaction temperature, the automated unit was stabilized for approximately one hour and the reactor effluent was sampled and analyzed. The product composition for these two reaction temperatures as ascertained by GC analysis and their respective reaction conditions for this example are listed in Table 1.

TABLE 1

| Conditions | | |
|---|---|---|
| Temperature (F) | 675 | 708 |
| WHSV (Hr-1) | 3 | 3 |
| H2/HC | 1 | 1 |
| Pressure (psig) | 270 | 270 |
| Yields (wt. %) | | |
| $C_5-$ | 1.1 | 2.2 |
| Benzene | 0.4 | 1.1 |
| Toluene | 8.6 | 15.9 |
| Para Xylene | 20.6 | 16.0 |
| Meta Xylene | 46.2 | 39.0 |
| Ortho Xylene | 17.6 | 16.0 |
| 1,2,4-Trimetbylbenzene | 4.9 | 7.4 |
| Total Trimethylbenzenes | 5.1 | 7.8 |
| Total Non-TMB $C_9+$ | 0.3 | 0.7 |
| Xylene Conversion (%) | 15.5 | 28.1 |
| Selectivity to 1,2,4-TMB (%) | 96.3 | 95.0 |
| Toluene/TMB (moiar ratio) | 2.1 | 2.4 |

The results listed above demonstrate that high pseudocumene selectivity can be achieved by the xylene disproportionation process according to the invention, while maintaining acceptable rates of xylene conversion (15.5% and 28.1%, as shown above). Although the feed was pure para xylene, the results show that xylene isomerization takes place over this catalyst. Thus a feed comprising mixed xylenes would give substantially similar results, given that xylene isomerization is taking place. Furthermore, as discussed above, a xylene isomerization catalyst placed above this bed would produce a mixed xylenes feed which would subsequently be converted to pseudocumene with a high selectivity via the xylene disproportionation process of the invention.

The results of Table 1 also demonstrate that the xylene disproportionation process of the present invention produces an effluent stream that can be easily processed by simple distillation to remove unconverted feed and other process by products and yield a high purity pseudocumene product.

What is claimed is:

1. A process for shape selective disproportionation of xylene comprising:

contacting a feed comprising xylene, under disproportionation conditions, with a surface modified ZSM-5 zeolite catalyst of which the surface is modified by contacting the ZSM-5 zeolite with a surface modifying agent selected from the group consisting of a selectivating compound containing silicon, a selectivating polymer containing silicon, a dicarboxylic acid, a bulky amine, a phosphine, a phenol, a polynuclear hydrocarbon, a cationic dye, a metal compound and a large complex cation, wherein said disproportionation selectively forms pseudocumene.

2. The process of claim 1 wherein said disproportionation process yields a product comprised of toluene, pseudocumene, mesitylene and hemimellitene, and pseudocumene selectivity is at least about 85 percent of total trimethylbenzenes.

3. The process of claim 2 wherein the pseudocumene selectivity is at least about 90 percent.

4. The process of claim 1 wherein said surface modification comprises from one to three steps of contacting the ZSM-5 zeolite with a surface modifying agent selected from the group consisting of a selectivating compound containing silicon and a selectivating polymer containing silicon.

5. The process of claim 4 wherein said at least one step is selected from ex-situ selectivation, in-situ selectivation, coking selectivation and combinations thereof.

6. The process of claim 1 wherein said xylene feed comprises ortho, meta and para-xylene and has a lower than equilibrium concentration of para-xylene.

7. The process of claim 1 further comprising the step of isomerizing the xylene feed to substantially equilibrium concentrations of ortho, meta and para-xylene, prior to contacting said xylene feed with said surface modified ZSM-5 catalyst to selectively form pseudocumene.

* * * * *